(12) United States Patent
Oakley et al.

(10) Patent No.: US 10,155,089 B2
(45) Date of Patent: Dec. 18, 2018

(54) DRUG DELIVERY DEVICE

(71) Applicant: Sanofi, Paris (FR)

(72) Inventors: Tom Oakley, Cambridge (GB); Karl Hewson, Cambridge (GB); Stuart Milne, Buckden St. Neots (GB); Mark Pawulski, Buckingham (GB)

(73) Assignee: Sanofi, Paris (FR)

( * ) Notice: Subject to any disclaimer, the term of this patent is extended or adjusted under 35 U.S.C. 154(b) by 338 days.

(21) Appl. No.: 14/905,393

(22) PCT Filed: Jul. 17, 2014

(86) PCT No.: PCT/EP2014/065339
§ 371 (c)(1),
(2) Date: Jan. 15, 2016

(87) PCT Pub. No.: WO2015/007820
PCT Pub. Date: Jan. 22, 2015

(65) Prior Publication Data
US 2016/0151580 A1    Jun. 2, 2016

(30) Foreign Application Priority Data

Jul. 17, 2013  (EP) .................................... 13176884

(51) Int. Cl.
*A61M 5/315*    (2006.01)
*A61M 5/24*     (2006.01)
(Continued)

(52) U.S. Cl.
CPC .......... *A61M 5/31551* (2013.01); *A61M 5/20* (2013.01); *A61M 5/24* (2013.01);
(Continued)

(58) Field of Classification Search
CPC ................ A61M 5/31551; A61M 5/24; A61M 5/31536; A61M 5/31541; A61M 5/31545; A61M 2005/31518; A61M 2005/3154
(Continued)

(56) References Cited

U.S. PATENT DOCUMENTS 5,112,317 A * 5/1992 Michel ..................... A61M 5/24
                                                      222/386
5,509,905 A * 4/1996 Michel .............. A61M 5/31553
                                                      604/207
(Continued)

FOREIGN PATENT DOCUMENTS

CN   102076372   5/2011
CN   102665802   6/2014
(Continued)

OTHER PUBLICATIONS

International Search Report and Written Opinion in International Application No. PCT/EP2014/065339 dated Oct. 11, 2014, 10 pages.
(Continued)

*Primary Examiner* — Manuel A Mendez
(74) *Attorney, Agent, or Firm* — Fish & Richardson P.C.

(57) ABSTRACT

A drug delivery device for selecting and dispensing a number of user variable doses of a medicament includes a housing, a cartridge holder for receiving a cartridge, a lead screw and means for driving the lead screw during dose dispensing. The lead screw is coupled to the cartridge holder such that the cartridge holder is axially displaced with respect to the housing and the lead screw during dose dispensing.

22 Claims, 5 Drawing Sheets (51) Int. Cl.
*A61M 5/20* (2006.01)
*A61M 5/31* (2006.01)

(52) U.S. Cl.
CPC .... *A61M 5/31536* (2013.01); *A61M 5/31541* (2013.01); *A61M 5/31545* (2013.01); *A61M 5/31553* (2013.01); *A61M 5/31583* (2013.01); *A61M 2005/3126* (2013.01); *A61M 2005/3154* (2013.01); *A61M 2005/31518* (2013.01)

(58) Field of Classification Search
USPC ................................ 604/211, 207, 151, 131
See application file for complete search history.

(56) References Cited

U.S. PATENT DOCUMENTS

2004/0054328 A1* 3/2004 Langley ............ A61M 5/14244
                                                                604/151
2009/0275914 A1 11/2009 Harms et al.

FOREIGN PATENT DOCUMENTS

| CN | 102802699 | 10/2014 |
|---|---|---|
| EP | 0897729 | 2/1999 |
| JP | H11-1999-104241 | 4/1999 |
| JP | 2009-502274 | 1/2009 |
| JP | 2013-512070 | 4/2013 |
| WO | WO 1993/016743 | 9/1993 |
| WO | WO 2002/051477 | 7/2002 |
| WO | WO 2004/078241 | 9/2004 |
| WO | WO 2007/017053 | 2/2007 |
| WO | WO 2009/132777 | 11/2009 |
| WO | WO 2010/123439 | 10/2010 |
| WO | WO 2011/053225 | 5/2011 |
| WO | WO 2011/068531 | 6/2011 |

OTHER PUBLICATIONS

International Preliminary Report on Patentability in International Application No. PCTEP2014065339 dated Jan. 19, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

DRUG DELIVERY DEVICE

TECHNICAL FIELD

This disclosure is generally directed to drug delivery devices for selecting and dispensing a number of user variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. Certain aspects of the present invention are not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. Certain aspects of the present invention are applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded during manufacture and springs which are loaded by the user during dose selecting. Some stored-energy devices use a combination of spring preload and additional energy provided by the user, for example during dose setting. In addition, there are further known forms of stored energy suitable for drug delivery devices, such as compressed gas, liquid-gas phase changes, chemical reactions (pyrotechnics), motors and solenoids with electrical power sources such as batteries. Certain aspects of the present invention are applicable for all of these types of devices, i.e. for devices with or without a drive spring or the like energy storage.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

SUMMARY

A disposable drug delivery device for selecting and dispensing a number of user variable doses of a medicament according to the some aspects of the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. The remaining dose in the cartridge is indicated to the user by the position of the bung and the distal end of the piston rod within the cartridge. Especially visually impaired users may find it difficult to identify the remaining dose in the cartridge.

Certain aspects of the invention provide improved drug delivery devices where the remaining dose will be more obvious to the user. It is a further object to make tampering and counterfeiting more difficult in a disposable drug delivery device.

According to a first embodiment of the present invention, a drug delivery device includes a housing, a cartridge holder for receiving a cartridge, a lead screw coupled to the cartridge holder and means for driving the lead screw during dose dispensing, wherein the cartridge holder is axially displaced with respect to the housing and the lead screw during dose dispensing. In other words, some aspects of the invention are based on the idea of retracting the cartridge with the cartridge holder instead of advancing the lead screw or piston rod. Thus, as the medication is used up the device length becomes shorter making it more apparent to the user when a device has little medication remaining or has been fully used. However, the bung and/or lead screw do not have to remain axially fixed relative to the housing. Moreover, in some embodiments the bung and/or lead screw may move axially in addition to the axial movement of the cartridge holder.

It is an additional benefit of retracting the cartridge, that it is more difficult to remove the cartridge holder from the housing when the cartridge is empty. This makes tampering and counterfeiting more difficult, and could make it impossible if the device is destroyed by removing the cartridge holder. Further, the device length is shorter at the end of use, so the device will take up less space in transport and disposal at the end of its useful life. This could also reduce the perceived environmental impact of disposal.

The lead screw may be coupled to the cartridge holder by a retraction nut which is axially constrained to the cartridge holder and in threaded engagement with the lead screw. The retraction nut may have an inner thread engaging an outer thread of the lead screw. Thus, rotation of the lead screw is converted into an axial movement (retraction) of the cartridge holder.

Independent of the above features, in certain aspects of the invention to provide a drug delivery device includes a housing, a cartridge holder and a lead screw which is axially constrained within the housing. This allows a simplified design of the lead screw and its attachment within the housing. As a consequence of the lead screw and thus the cartridge bung being axially fixed within the housing during dispensing, the glass ampoule of the cartridge has to be displaced relative to the bung and the housing.

Preferably, the cartridge holder is slidably guided in the housing and rotationally constrained to the housing. For example, a bush bearing or floating bearing may be provided for displaceably receiving the cartridge holder. In addition or as an alternative, the retraction nut may be slidably guided in the housing and rotationally constrained to the housing, with the cartridge holder being axially and rotationally constrained to the retraction nut.

To reduce the dispensing force a user has to apply, the drug delivery device may further comprise an elastic element such as a spring for driving the lead screw during dose dispensing. In a disposable device, the spring may be a preloaded spring, i.e. a factory preloaded spring charged for the lifespan of the device. As an alternative, e.g. for a reusable device, the spring may be loaded during dose setting and releases the stored energy during dose dispensing. Either a disposable or a reusable device may use a combination of factory-set preload and user-generated load of the spring. Typical spring types suitable for a drug delivery device include a torsion spring, a tension spring or the like.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of U300 (where U300 means 300 IU/mL) insulin formulation, may be limited to avoid overdosage. Preferably, the limits for the minimum dose and the maximum dose are provided by hard stop features.

The limiter mechanism may comprise a first member, e.g. a sleeve, which is rotatable during dose setting and dose dispensing and which is coupled to a dose setting member and/or to a drive member, and a second member, e.g. a nut, coupled to the first member and to the housing such that the second member is moved along a track, whose ends define the maximum dose position and the minimum dose position, with respect to the first member and/or the housing if the first member rotates. Preferably, the track is a thread or a spline in the interface between the sleeve and the nut.

To prevent an underdosage or a malfunction, the drug delivery device may comprise a last dose protection mechanism for preventing the setting of a dose, which exceeds the amount of liquid left in a cartridge. In a preferred embodiment, this last dose protection mechanism only detects the medicament remaining in the cartridge when the cartridge contains less than the maximum dose (e.g. 120 IU of insulin formulation). For example, the last dose protection mechanism comprises the second member (nut) of the limiter mechanism and a member, preferably the cartridge retraction nut or the cartridge holder, which is moved in the proximal direction during dose dispensing. This proximally moving member abuts the nut of the limiter mechanism as soon as the set dose equals the amount of dispensable liquid left in a cartridge to prevent further dose setting.

In a further embodiment, the drug delivery device comprises a display for indicating the selected dose. The display may have symbols, colours or texture for indicating the selected dose and is usually visible through an aperture or window of the housing.

Known devices often include a number sleeve running on a helix relative to the housing which results in the number sleeve moving axially which can make the device longer. Further, the minimum axial movement is limited due to requirements on the minimum text size and the maximum number of doses which must be supported. Devices with a large number of doses will require large axial displacements of the number sleeve, and it is difficult to prevent numbers being shown outside the dose indicator window, for example on the barrel of the number sleeve.

To overcome such drawbacks, the display comprises at least one dose indicating element which is rotatable but axially constrained in the housing. An embodiment includes an 'odometer' dose indicator which only rotates, i.e. it does not move axially. Preferably the display comprises a first dose indicating element (first scale or single units wheel) and a second dose indicating element (second scale or tens wheel), with the first dose indicating element being coupled to the second dose indicating element such that a continuous rotation of the first dose indicating element is translated into an intermittent rotation of the second dose indicating element. In more detail, as the dose number is increased or reduced by rotating a dosage selector the first dose indicating element is entrained. A flexible 'arm' element of the first dose indicating element may run along a cam profile such that each time the dose selector is rotated for example 180° the flexible 'arm' element becomes engaged with the second dose indicating element, i.e. the tens wheel, and indexes this wheel by one digit.

The drug delivery device may comprise at least one clicker mechanism for generating a haptic and/or audible feedback. Preferably, the clicker mechanism signifies the end of dose dispensing. In addition or as an alternative the clicker mechanism generates a different feedback when dialling single units or multiples of 10 units. In other words, the user hears or feels a harder 'click' when the set dose passes a multiple of 10 units than when it passes other units.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-GlyGlu-Gly-Thr-Phe-Thr-Ser-Asp-Leu-Ser-Lys-Gln-Met-Glu-Glu-Glu-Ala-Val-Arg-LeuPhe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)(Lys)6-NH2,
H-Asn-(Glu)5-des Pro36, Pro37, Pro38 [Met(O)14, Trp(O2)25, Asp28] Exendin-4(1-39)-(Lys)6-N H2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

A non-limiting, exemplary embodiment of the invention will now be described with reference to the accompanying drawings, in which.

DETAILED DESCRIPTION

Figure 1:
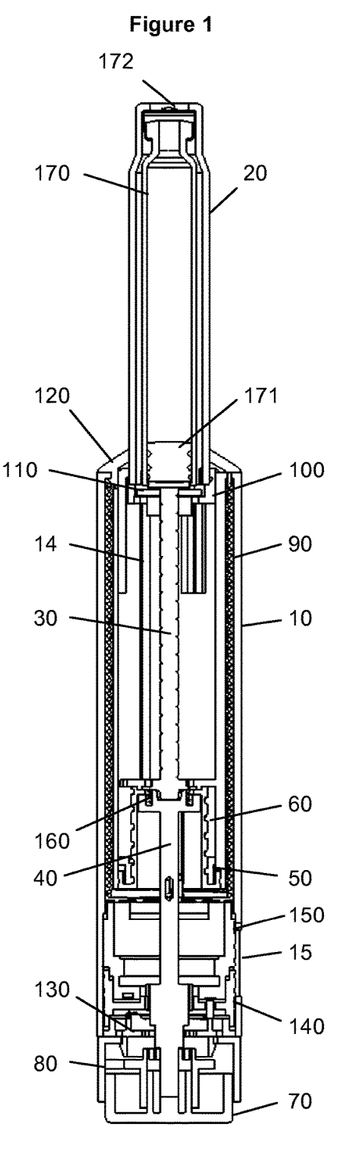
FIG. 1 shows a sectional view of a drug delivery device in accordance with the present invention.
Figure 2:
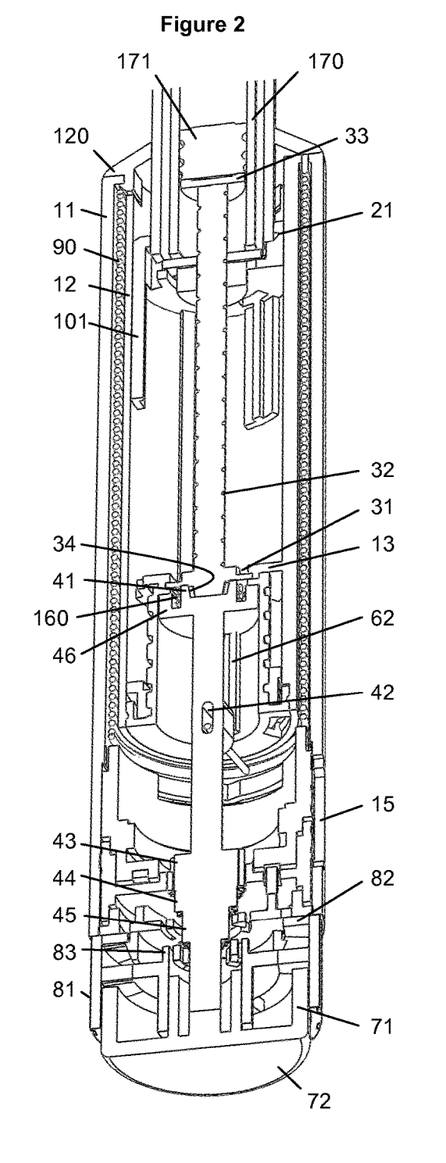
FIG. 2 shows an enlarged sectional view of the drug delivery device of FIG. 1.
Figures 3, 5:
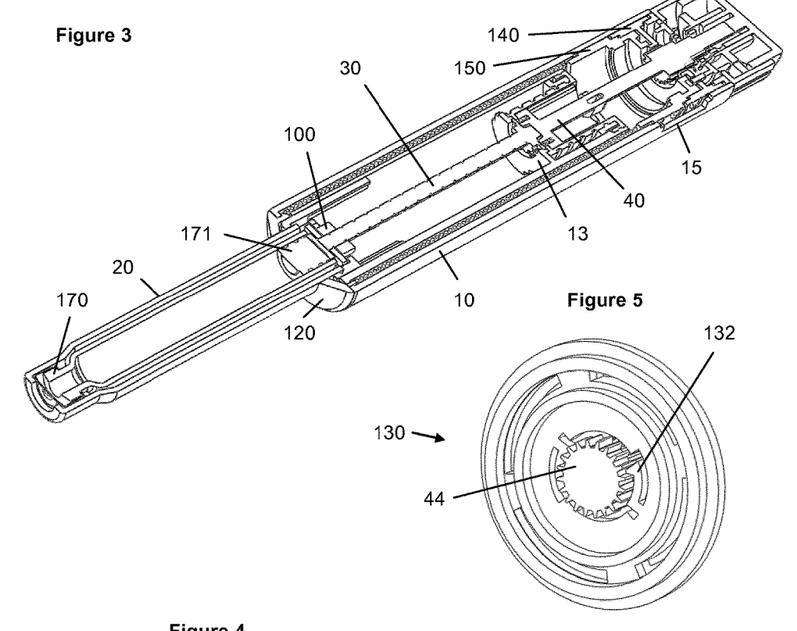
FIG. 3 shows a further sectional view of the drug delivery device of FIG. 1.
FIG. 5 shows cut-away views of a detail of the drug delivery device of FIG. 1.
Figure 4:
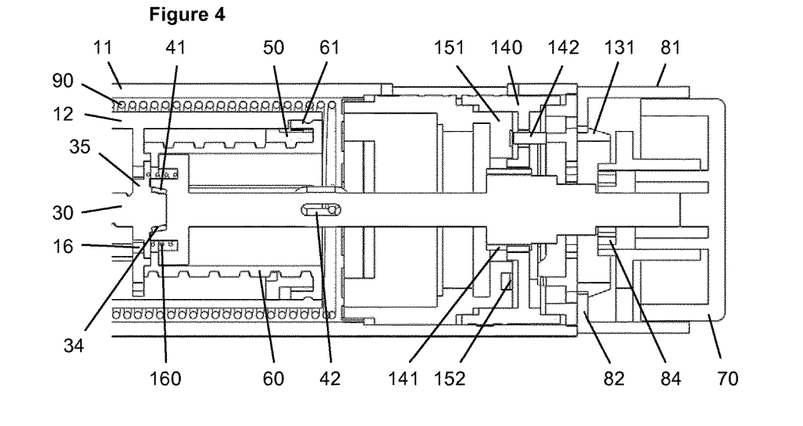
FIG. 4 shows a further enlarged sectional view of the drug delivery device of FIG. 1.

FIG. 1 shows a drug delivery device in the form of an injection pen. The device has a distal end (upper end in FIG. 1) and a proximal end (lower end in FIG. 1). The component parts of the drug delivery device are shown in FIGS. 2 to 4 in more detail. The drug delivery device comprises a housing 10, a cartridge holder 20, a lead screw (piston rod) 30, a driver 40, a restriction nut 50, a sleeve 60, a button 70, a dose selector 80, a torsion spring 90, a retraction nut 100, a disk (anti backlash element) 110, a bezel 120, a chassis 130, a first scale 140, a second scale 150, a return spring 160 and a cartridge 170. A needle arrangement (not shown) with a needle hub and a needle cover may be provided as additional components, which can be exchanged as explained above.

The (outer) housing 10 is a generally tubular element. In the embodiment shown in the figures, the housing 10 is a double-walled housing having an outer housing wall 11 and an inner housing wall 12 which are connected at the distal end of housing 10. Thus, an annular space is provided between outer wall 11 and inner wall 12. As will be explained below, torsion spring 90 is located in this annular space. The inner wall 12 is provided with an inwardly protruding flange 13 with a central opening. Further, the inner surface of inner wall 12 is provided with ribs 14 which extend in the axial (longitudinal) direction of the housing 10. A window 15 or an aperture is located in the proximal region of the housing 10. A transparent or translucent insert (not shown in the figures) may be provided in the window aperture 15. As an alternative to the embodiment depicted in the figures, outer wall 11 and inner wall 12 of the housing 10 may be provided as separate components which might be useful for manufacturing reasons. A flexible finger 16 is arranged inside flange 13 to cooperate with a ratchet or clicker feature of lead screw 30.

Figure 17:
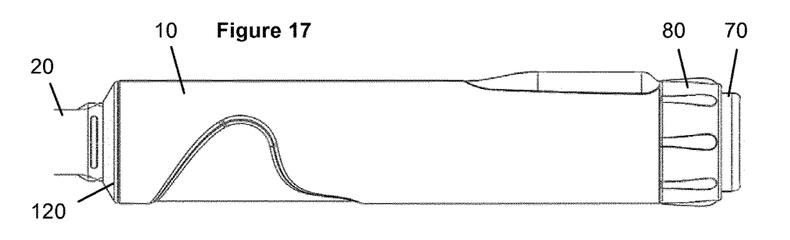
FIG. 17 shows a side view of the drug delivery device of FIG. 1.

The cartridge holder 20 is located at the distal side of housing 10. The cartridge holder may be a transparent, translucent or opaque component which is tubular to receive cartridge 170. The distal end (upper end in FIG. 1) of cartridge holder 20 may be provided with means for attaching a needle arrangement. As will be explained in more detail below, the cartridge holder 20 is not rigidly fixed to housing 10, but may be retracted into housing 10. FIGS. 1 and 3 show the fully extended position of cartridge holder 20, whereas FIG. 17 shows the fully retracted position of cartridge holder 20, where only the necked-down distal end of cartridge holder 20 protrudes from housing 10. The cartridge holder 20 is provided with snap-hooks 21 for attaching cartridge holder 20 to retraction nut 100.

The lead screw 30 is an elongate member which—in the present embodiment—is axially fixed within the device. This is achieved by a proximal flange 31 engaging inner flange 13 of housing 10. Lead screw 30 may be an injection moulded plastic component, for example made from ABS, or a metal component. An outer thread 32 is provided on lead screw 30. The distal end of lead screw 30 may be provided with a bearing 33 which may have the form of a disc rotatable with respect to the lead screw 30. The proximal end of lead screw 30 is provided with a ring of teeth 34 (face gear) located near flange 31. Lead screw 30 has a ring of teeth 35 near its proximal end. Teeth 35 interact with finger 16 of housing 10 forming a clicker ratchet providing haptic and audible feedback during dose dispensing.

In an alternative embodiment (not shown) the bung of cartridge 170 and/or lead screw 30 are allowed to move axially, in addition to the axial movement of the cartridge 170. This axial movement may be opposite to the movement of the cartridge 170, i.e. increasing the dispensing stroke, or in the same direction as the cartridge movement but with a different speed, thus reducing the dispensing stroke.

Figure 15:
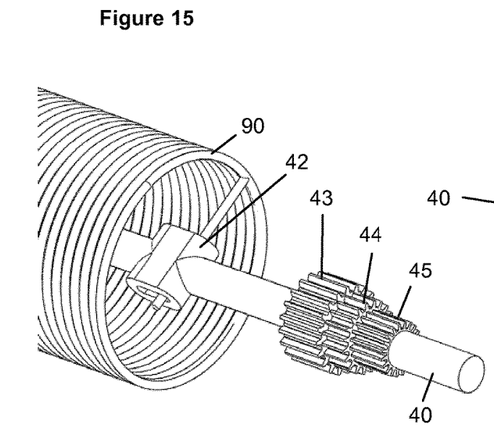
FIG. 15 shows a perspective view of a detail of the drug delivery device of FIG. 1.

The driver 40 is a rod located in the proximal region of the device. Driver 40 has at its distal end teeth 41 (a face gear in this embodiment, but could be internal or external teeth of a spur gear) for engaging teeth 34 of lead screw 30. Driver 40 is rotatable within housing 10 and may be shifted in the axial direction. FIG. 2 shows the distal position of driver 40, where teeth 34 of the lead screw 30 engage with teeth 41 of the driver, whereas FIG. 4 shows the proximal position of driver 40, where teeth 34 and 41 are disengaged. An aperture 42 is provided in the driver 40 for receiving one end of torsion spring 90. As can be seen in FIGS. 2 and 4, aperture 42 is provided as a slot to allow axial movement of driver 40 without deflecting the free end of torsion spring 90. Further, three gear pinions 43, 44, 45 are located on driver 40. Gear pinions 43, 44, 45 may be separate components which are rigidly attached to the driver rod, however it is preferred to mould the rod and the gear pinions as a unitary component. As can be seen in FIG. 15, gear pinions 43, 44, 45 may have a different diameter and a different number of teeth. At its distal end, driver 40 carries a flange 46 which is splined to sleeve 60.

Figure 13:
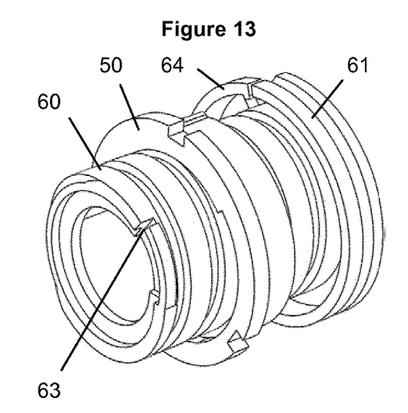
FIG. 13 shows a cut-away view of a detail of the drug delivery device of FIG. 1.
Figure 14:
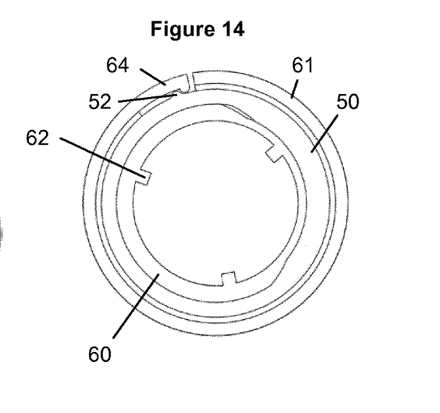
FIG. 14 shows a sectional view of a detail of the drug delivery device of FIG. 1.

The restriction nut 50 is a sleeve-like component with an inner thread engaging sleeve 60. Further, restriction nut 50 is splined to the inner surface of inner wall 12 to prevent relative rotation between restriction nut 50 and housing 10 while allowing relative axial movement of restriction nut 50 with respect to housing 10. In the embodiment shown in FIG. 6, restriction nut 50 is provided with grooves 51 engaging corresponding ribs at the inner surface of inner wall 12. As shown in FIGS. 13 and 14, a detent 52 or protrusion is provided on the outer surface of restriction nut 50 for engaging an end of dose feature of sleeve 60.

The sleeve 60 is a tubular dose restriction element. As can be seen in the enlarged detail of FIG. 4, sleeve 60 has a proximal flange 61 which is snapped into inner wall 12 of housing 10 such that sleeve 60 is axially constrained to housing 10 but rotatable with respect to housing 10. Sleeve 60 has an outer thread engaging the inner thread of restriction nut 50. At its inner surface, sleeve 60 is provided with ribs 62 (see FIG. 14) engaging corresponding grooves in flange 46 of driver 40. Thus, sleeve 60 is rotationally constrained to driver 40 but allows axial displacement of driver 40 with respect to sleeve 60. The distal end face of sleeve 60 abuts flange 13 of housing 10 and a flange portion at the distal end of sleeve 60 contacts flange 31 of lead screw 30 to constrain lead screw 30 axially within the device. Rotational hard stops 63 are provided at either end of the outer thread of sleeve 60 to restrict movement of restriction nut 50 with respect to sleeve 60. A finger 64 with a hook-like end is provided within flange 61. Finger 64 is located such that detent 52 of restriction nut 50 contacts and deflects finger 64 shortly before or when the proximal rotational hard stop is reached.

The button 70 forms the proximal end of the device. Button 70 has an annular skirt 71 received within dose selector 80. Further, button 70 has a central stem 72 which abuts the proximal end face of driver 40.

Figure 16:
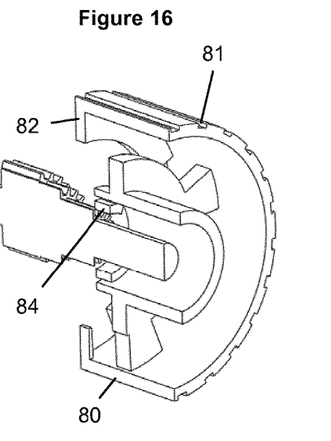
FIG. 16 shows a cut-away view of a detail of the drug delivery device of FIG. 1.

The dose selector 80 is a sleeve-like component with a serrated outer skirt 81. A flange 82 is provided protruding inwardly at the distal end of dose selector 80 to provide a snap connection with chassis 130. Further, dose selector 80 is provided with an inner sleeve 83 having a ratchet feature 84 which engages gear pinion 45 of driver 40 (see FIG. 16). Ratchet feature 84 may be made as an over ratchet providing haptic and audible feedback if restriction nut 50 reached one of the rotational heard stops of sleeve 60.

As mentioned above, the torsion spring is located between the outer wall 11 and the inner wall 12 of housing 10. The distal free end of torsion spring 90 engages housing 10. The proximal free end of torsion spring 90 engages aperture 42 of driver 40 as explained above. Thus, a relative rotation between driver 40 and housing 10 winds or unwinds torsion spring 90.

The retraction nut 100 is an annular element having a distal end for receiving snap hooks 21 of the cartridge holder such that the cartridge holder 20 is permanently attached to retraction nut 100. Alternative embodiments may include a releasable attachment of cartridge holder 20 with retraction nut 100. A central aperture of retraction nut 100 is provided with an inner thread engaging outer thread 32 of lead screw 30. The retraction nut 100 has an outer surface which is guided within the inner wall 12 of housing 10. This outer surface includes in the embodiment shown in the figures three arms 101 which extend in the proximal direction of retraction nut 100. Further, grooves 102 are provided in the outer surface of retraction nut 100 which engage ribs 14 of the inner surface of inner wall 12. Thus, retraction nut 100 is rotationally constrained to housing 10 but is free to slide axially within housing 10.

The disc 110 is provided at the distal end of lead screw 30 and serves as an anti-backlash element improving the alignment of cartridge holder 20 with respect to the housing 10.

The bezel 120 is located at the distal end of housing 10. Bezel 120 is snapped onto housing 10 and comprises an opening for receiving and guiding cartridge holder 20. Thus, bezel 120 forms a bush bearing or floating bearing for the cartridge holder 20.

The chassis 130 is rigidly attached to housing 10 and axially and rotationally constrained within housing 10. Chassis 130 is provided with snap arms 131 for attaching dose selector 80 via its flange 82. Chassis 130 is provided with a central aperture receiving driver 40. Ratchet fingers 132 are provided on an inner surface of chassis 130 which engage gear pinion 44 of driver 40. Ratchet fingers 132 are designed such that a relative rotation of driver 40 with respect to chassis 130 is allowed during dose setting and dose correction. However ratchet fingers 132 couple driver 40 via gear pinion 44 to the housing 10 such that torsion spring 90 cannot overcome this ratchet. In other words, ratchet finger 132 and gear pinion 44 prevent unwinding of torsion spring 90. This ratchet may act as a clicker ratchet providing haptic and audible feedback during dose setting and dose correction. A distal face of chassis 130 is provided with a cam profile 133 interacting with a feature of the first scale member 140.

The first scale member 140 is a tubular element which is rotatably guided within housing 10. First scale 140 has an inwardly directed flange with teeth 141 which engage gear pinion 43 of driver 40. Thus, the first scale member 140 is rotationally constrained to driver 40 but allows axial displacement of the driver 40. The outer surface of the first scale 140 is provided with numbers or the like elements for indicating a set dose to a user. At least a portion of this outer surface is visible through window aperture 15 in housing 10. A flexible finger 142 is provided in the flange-like wall of the first scale 140. This finger 142 interacts with cam profile 133 of chassis 130 as the first scale 140 rotates with respect to chassis 130. In other words, finger 142 is deflected by cam profile 133 in the distal direction. The cam profile 133 is designed such that finger 142 is mainly held in its substantially unstressed (proximal) position and is deflected only twice per revolution in its distal position. Thus, two ramps are provided on cam profile 133 which are evenly distributed. In its deflected distal position, finger 142 engages a corresponding feature of the second scale 150 to entrain second scale 150 as the first scale 140 rotates. A detent feature 143 may provide haptic and audible feedback during dose setting and dose correction. The first scale member 140 forms the "1s" (Units) dose wheel of the device.

Second scale 150 is a substantially tubular element having an inwardly protruding flange 151 at its proximal end. Second scale 150 is rotatably guided within housing 10 and positioned such that at least a part of the outer surface of second scale 150 is visible through window aperture 15 of housing 10. Numbers or the like may be printed on this outer surface of second scale 150. Flange 151 is provided with recesses or a face gear 152 which is positioned such that a protrusion of a flexible finger 142 engages face gear 152 in the deflected distal position of finger 142. However, in the unstressed proximal position of finger 142 face gear 152 is decoupled from finger 142 such that first scale 140 may rotate relative to second scale 150. A detent feature 153 may provide haptic and audible feedback during dose setting and dose correction. The second scale member 150 forms the "10s" (Units) dose wheel of the device.

The return spring 160 is located between flange 31 of lead screw 30 and flange 46 of driver 40. As flange 31 rests on flange 13 of housing 10, return spring 160 biases driver 40 in the proximal direction as shown in FIG. 4. By pressing button 70, driver 40 is displaced in the distal direction thus compressing return spring 160.

The cartridge 170 is received in cartridge holder 20. The cartridge 170 may be a glass ampule having a moveable rubber bung 171 at its proximal end. The distal end of cartridge 170 is provided with a pierceable rubber seal 172 which is held in place by a crimped annular metal band. In the embodiment depicted in the figures, the cartridge 170 is a standard 1.5 ml cartridge. The device is designed to be disposable in that the cartridge 170 cannot be replaced by the user or health care professional. However, a reusable variant of the device could be provided by making the cartridge holder 120 removable and allowing the resetting of retraction nut 100.

In the following, the functioning of the disposable drug delivery device and its components will be explained in more detail.

When the device is at rest as shown in FIG. 3 the torsion spring 90 has enough preload such that if the user selects the minimum dose the device will be able to deliver that minimum dose. At rest the dose indicator (scales 140, 150) displays 0 or the equivalent marking to show that no dose has been selected.

Priming is the act of preparing the device for first use. In existing pen injectors this means setting and delivering one or more small doses into air so that the 'play' (any clearances) and tolerances in the device are removed and that components are placed into suitable compression or tension. Safety shots are where the user sets and delivers one or more small doses into air before each injection to ensure that the needle is not blocked. In the embodiment depicted in the Figures, there are no specific features that make the priming or safety shot requirements different to those of existing pen injectors. For both priming the device and for safety shots, the user will set small dose and inject that dose into air and repeat until a drop of medicament is observed at the tip of the needle.

The user sets a dose by rotating the dosage selector 80. Rotating the dosage selector rotates the driver 40 and adds preload to the torsion spring 90. The driver 40 is splined to first scale 140 and indexes when the user dials the dosage selector 80.

As shown in FIG. 5, the spline features (gear pinion 44) on the driver 40 engage with ratchet finger 132 on the chassis 130 to prevent the dosage selector 80 rotating back to its initial position due to the torsion spring torque. These ratchet features becomes disengaged when the user fully depresses the injection button 70.

Figure 9:
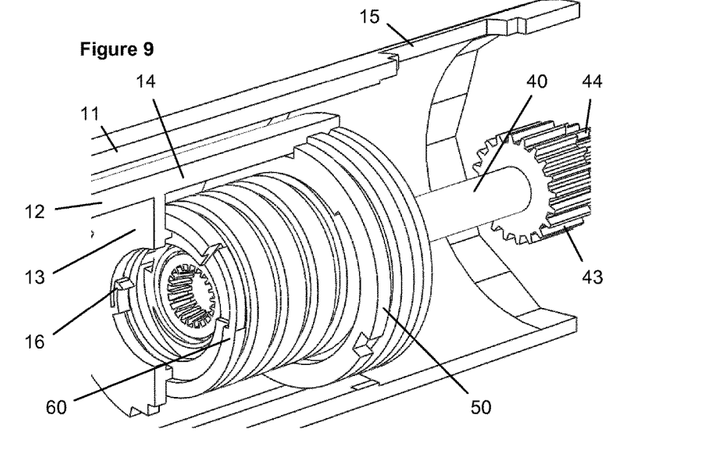
FIG. 9 shows a cut-away view of a detail of the drug delivery device of FIG. 1.

Limits for setting the minimum and maximum dose (0 IU and 120 IU of U300 insulin in this embodiment) are provided by hard stop features on the dose restriction nut 50 (FIGS. 9 and 12) which interfere with features on the dose restriction sleeve 60 and therefore prevent further relative rotation. During dialling and injection the dose restriction nut 50 is moved up and down the thread on the dose restriction sleeve 60.

A last dose protection prevents the user from setting a dose greater than the available volume in the cartridge 170. Many pen injectors use a threaded nut or half nut mechanism to achieve a last dose protection. Typically these mechanisms operate across the entire volume of the cartridge e.g. 3 ml for a 300 IU, U100 insulin cartridge. On some devices it is possible for the user to over-tighten the protection mechanism resulting in device jamming.

The embodiment of the retracting cartridge features the cartridge retraction nut 100 which is drawn in to the device as the medication is used up. When there is less than the maximum dose remaining in the cartridge, the cartridge retraction nut 100 becomes engaged with the dose restriction nut 50 forming a rotary or an axial hard stop with the dose restriction sleeve. In other words, the device only detects the medicament remaining in the cartridge 170 when the cartridge contains less than the maximum dose (120 IU of U300 insulin formulation in this case).

Figures 10, 11, 12:
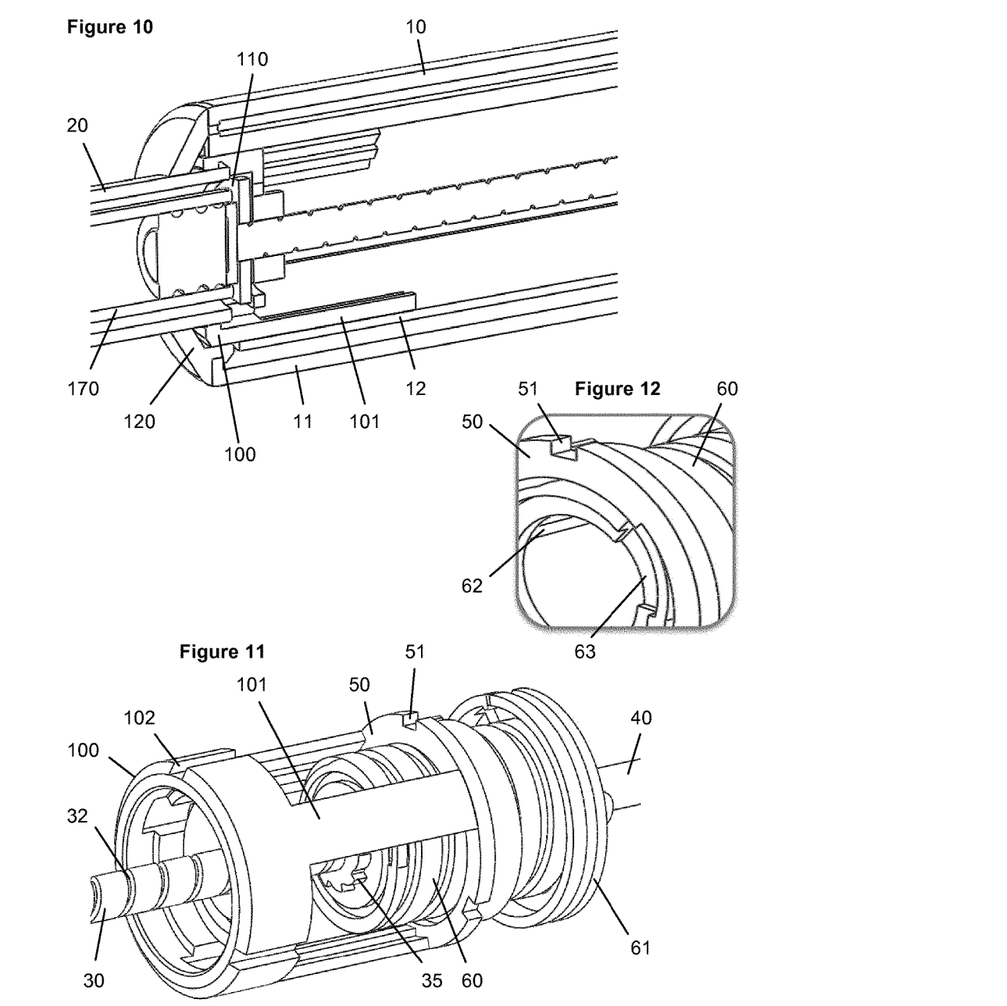
FIG. 10 shows a further enlarged sectional view of the drug delivery device of FIG. 1.
FIG. 11 shows a cut-away view of a detail of the drug delivery device of FIG. 1.
FIG. 12 shows a cut-away view of a detail of the drug delivery device of FIG. 1.

During injection, the driver 40 is engaged with the lead screw 30. The cartridge retraction nut 100 is threaded to the lead screw 30 and splined to the housing 10 such that as the injection is delivered the cartridge retraction nut 100 is drawn in to the housing 10. When the cartridge volume falls below the maximum settable dose (120 IU of U300 insulin formulation in this embodiment) the cartridge retraction nut 100 has moved in to a position where it can interfere with the dose restriction nut 50. When the user attempts to dial a dose greater than that remaining, the dose restriction nut 50 interferes with the arms 101 of the cartridge retraction nut 100 to form an axial hard stop as shown in FIG. 11. As an alternative, it is also possible to adapt these features to form a rotary hard stop.

Most pen injectors have a dose indicator which displays the set dose to the user, and counts down to zero as the dose is dispensed. Most pen injectors also feature the rotation of at least one component to set the dose. The dose is normally delivered by converting the rotational movement of setting the dose into translation movement of the bung 171 in the cartridge 170. Therefore most pen injectors feature a number sleeve with dose indications on it which moves on a helix relative to the housing. The problems with running the number sleeve on a helix relative to the housing are that the number sleeve moves axially which can make the device longer. Further, the minimum axial movement is limited due to requirements on the minimum text size and the maximum number of doses which must be supported. Devices with a large number of doses will require large axial displacements of the number sleeve, and it is difficult to prevent numbers being shown outside the dose indicator window, for example on the barrel of the number sleeve. The geometry of the text is tied to the geometry of the drive mechanism. This can limit text size or require large displacements for dose setting and injection.

Figures 6, 7, 8:
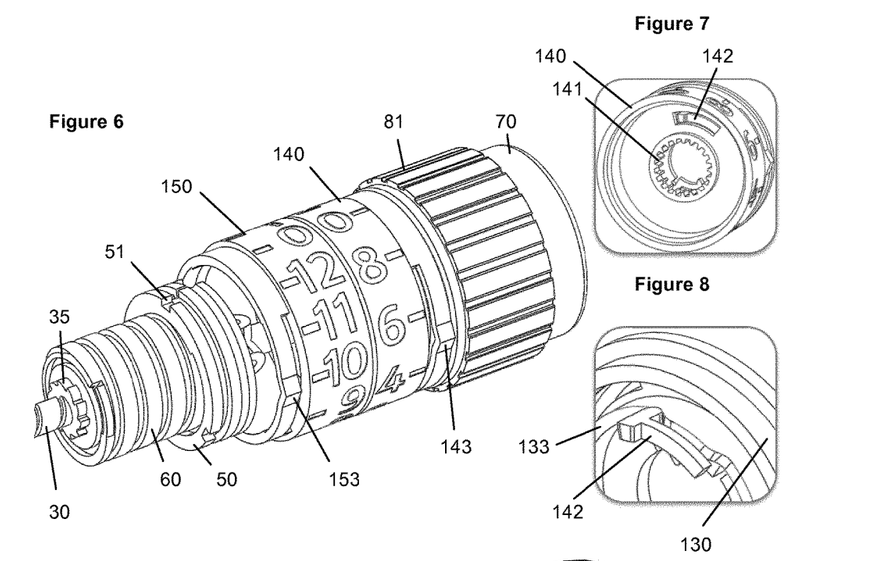
FIG. 6 shows a cut-away view of a further detail of the drug delivery device of FIG. 1.
FIG. 7 shows a cut-away view of a detail of the drug delivery device of FIG. 1.
FIG. 8 shows a cut-away view of a detail of the drug delivery device of FIG. 1.

To overcome such drawbacks, the embodiment of the retracting cartridge includes an 'odometer' dose indicator which only rotates, i.e. it does not move axially. In more detail, the dose number is increased or reduced as the dosage selector 80 is rotated. This is achieved via a spline feature (gear pinion 43 and teeth 141) between the first scale member 140 and the driver 40. The flexible 'arm' element (finger 142) within the first scale member 140 runs along the cam profile 133 on the chassis 130. Each time the dose selector 80 is rotated 180° the finger 142 becomes engaged with the second scale member 150, i.e. the tens wheel, and indexes this wheel by one digit. This is depicted in FIGS. 6 to 8.

Most known injector pens feature a uniform level of feedback when setting the dose, that is, the user perceives no change in sensation whether dialling 9 units or 10 units. This results in greater dependency on patient visual acuity and ability to process the numerical information shown by the dose indicator. In contrast to that with some aspects of the present invention the patient will perceive different feedback when dialling single units or multiples of 10 units. The embodiment shown allows that the user hears or feels a harder 'click' when the set dose passes a multiple of 10 units than when it passes other units. As mentioned above, both the first and second scale members 140, 150 include detent features 143, 153 which engage with corresponding elements on the inside of the housing 10. These elements are designed such that as each wheel 140, 150 indexes the patient will perceive a different level of haptic and audible feedback. For example, the first scale member 140 (units wheel) might have a light detent whereas the second scale member 150 (tens wheel) may have a heavy detent.

When the injection button 70 is pressed the following actions take place: The driver 40 is moved forward by the injection button 70, which compresses the return spring 160, and engages with the lead screw 30. The driver 40 disengages from the dosage selector 80 (ratchet 84) which may now be rotated freely without influencing the injection or the set dose. The driver 40 moves off its ratchet (finger 132) to the chassis 130 so it is free to rotate. The torsion spring 90 begins to unwind rotating the driver 40 which in turn rotates the lead screw 30. As the lead screw 30 rotates the cartridge retraction nut 100 is drawn in to the housing 10 dispensing the medication.

If the axial force on the injection button 70 is removed, the button 70 returns to its initial axial position relative to the dosage selector 80 and this allows the ratchets on the driver 40 to engage with the chassis 130, thus preventing further injection due to the driving torque of the torsion spring 90. Further, this reengages the driver 40 with the dosage selector 80 thus allowing the dosage selector to set the dose again. The dose can be changed by rotating the dosage selector 80 and pressing the injection button 70 restarts the injection manoeuvre.

Currently most injector pens have a cartridge holder fixed rigidly to the device body. In these devices the elastomeric bung in the cartridge is progressed forward by a lead screw to dispense the contents. Certain aspects of the present invention feature a lead screw 30 fixed axially within the device. When the lead screw 30 rotates during injection the cartridge holder 20 is drawn inside the housing 10. In this case it is the bung 171 which remains fixed axially and it is the cartridge 170 which moves (with the cartridge holder 20) to dispense the injection.

One of the benefits offered by retracting the cartridge 170 in to the device housing 10 is that the remaining dose will be more obvious to the user. As the medication is used up the device length becomes shorter making it more apparent to the user when a device has little medication remaining or has been fully used. In addition, it should be more difficult to remove the cartridge holder 20 from the housing 10. This makes tampering and counterfeiting more difficult, and could make it impossible if the device is destroyed by removing the cartridge holder 20. Further, the device length is shorter at the end of use, so the device will take up less space in transport and disposal at the end of its useful life. This could also reduce the perceived environmental impact of disposal.

During injection the torsion spring 90 unwinds, rotating the driver 40. This will index the dose number mechanism such that the number counts down towards zero. At the same time the dose restriction nut 50 moves back towards its zero position shown in FIG. 9. When the dose restriction nut 50 has reached this position the user will hear and possibly feel a "click" to signify end of dose. This is achieved by features 52 and 64 on the dose restriction nut 50 and the dose restriction sleeve 60 passing over each other with slight detent interference (FIGS. 13 and 14).

The invention claimed is:

1. A drug delivery device for selecting and dispensing a number of user variable doses of a medicament, the drug delivery device comprising:
    a housing;
    a cartridge holder for receiving a cartridge;
    a lead screw; and
    a drive mechanism configured to drive the lead screw during dose dispensing, the lead screw being coupled to the cartridge holder such that the lead screw rotates relative to the housing without translating axially within the housing during the dose dispensing and such that the cartridge holder is axially displaced with respect to the housing and the lead screw during the dose dispensing.

2. The drug delivery device of claim 1, wherein the lead screw is coupled to the cartridge holder by a retraction nut which is axially constrained to the cartridge holder and in threaded engagement with the lead screw.

3. The drug delivery device of claim 2, wherein the retraction nut is slidably guided in the housing and rotationally constrained to the housing, and wherein the cartridge holder is axially and rotationally constrained to the retraction nut.

4. The drug delivery device of claim 1, wherein the lead screw is axially constrained within the housing.

5. The drug delivery device of claim 1, wherein the cartridge holder is slidably guided in the housing and rotationally constrained to the housing.

6. The drug delivery device of claim 1, wherein the drive mechanism comprises a spring configured to drive the lead screw during the dose dispensing.

7. The drug delivery device of claim 6, wherein the spring is a torsion spring, and the drive mechanism further comprises a driver comprising teeth engaged with the lead screw, the torsion spring being engaged with the driver.

8. The drug delivery device of claim 1, comprising a limiter mechanism defining a maximum settable dose and a minimum settable dose.

9. The drug delivery device of claim 8, wherein the limiter mechanism comprises:
    a first member, which is rotatable during dose setting and the dose dispensing and which is coupled to at least one of a dose setting member and a drive member, and
    a second member coupled to the first member and to the housing such that the second member is moved along a track with respect to at least one of the first member and the housing if the first member rotates, wherein ends of the track define the maximum settable dose and the minimum settable dose.

10. The drug delivery device of claim 9, further comprising a last dose protection mechanism for inhibiting setting of a dose exceeding an amount of liquid left in the cartridge, wherein the last dose protection mechanism comprises the second member of the limiter mechanism and a member configured to move in a proximal direction during the dose dispensing.

11. The drug delivery device of claim 1, comprising a last dose protection mechanism for inhibiting setting of a dose exceeding an amount of liquid left in the cartridge.

12. The drug delivery device of claim 1, comprising a display for indicating a set dose.

13. The drug delivery device of claim 12, wherein the display comprises at least one dose indicating element rotatable relative to the housing but axially constrained in the housing.

14. The drug delivery device of claim 13, wherein the display comprises a first dose indicating element and a second dose indicating element, wherein the first dose indicating element is coupled to the second dose indicating element such that a continuous rotation of the first dose indicating element is translated into an intermittent rotation of the second dose indicating element.

15. The drug delivery device of claim 1, comprising at least one clicker mechanism for generating a feedback indicating an end of the dose dispensing, the feedback being at least one of a haptic feedback and an audible feedback.

16. The drug delivery device of claim 1, comprising at least one clicker mechanism for generating a first feedback when dialing single units of the medicament to be delivered, and a second feedback different from the first feedback when dialing multiples of 10 units of the medicament to be delivered, the first feedback and the second feedback each being at least one of a haptic feedback and an audible feedback.

17. The drug delivery device of claim 1, further comprising the cartridge containing the medicament.

18. A method of operating a drug delivery device, the method comprising:
    setting a dose of a medicament to be delivered; and
    dispensing the dose of the medicament by causing a lead screw to rotate relative to a housing of the drug delivery device without causing the lead screw to translate axially within the housing of the drug delivery device.

19. The method of claim 18, wherein dispensing the dose of the medicament comprises pushing an injection button to release a torsion spring to cause the lead screw to rotate.

20. The method of claim 18, wherein setting the dose comprises rotating a dosage selector to add preload to a torsion spring that, upon release, causes the lead screw to rotate.

21. The method of claim 18, wherein dispensing the dose of the medicament causes the lead screw to rotate relative to the housing of the drug delivery device such that a bung remains axially fixed relative to the housing while a cartridge containing the bung moves axially relative to the housing.

22. A method of operating a drug delivery device, the method comprising:
  setting a dose of a medicament to be delivered; and
  dispensing the dose of the medicament by causing a lead screw to rotate relative to a housing of the drug delivery device such that a cartridge holder is axially displaced with respect to a housing and with respect to the lead screw.

* * * * *

UNITED STATES PATENT AND TRADEMARK OFFICE
CERTIFICATE OF CORRECTION

PATENT NO.        : 10,155,089 B2
APPLICATION NO.   : 14/905393
DATED             : December 18, 2018
INVENTOR(S)       : Tom Oakley et al.

Page 1 of 1

It is certified that error appears in the above-identified patent and that said Letters Patent is hereby corrected as shown below:

In the Specification

In Column 1, Line 2, below "DRUG DELIVERY DEVICE" insert:
-- CROSS-REFERENCE TO RELATED APPLICATIONS
This application is a U.S. national stage application under 35 USC § 371 of International Application No. PCT/EP2014/065339, filed on July 17, 2014, which claims priority to European Patent Application No. 13176884.8, filed on July 17, 2013, the entire contents of which are incorporated herein by reference. --

Signed and Sealed this
Twenty-eighth Day of May, 2019

Andrei Iancu
*Director of the United States Patent and Trademark Office*